United States Patent [19]

Kramer et al.

[11] Patent Number: 5,112,734
[45] Date of Patent: May 12, 1992

[54] TARGET-DEPENDENT SYNTHESIS OF AN ARTIFICIAL GENE FOR THE SYNTHESIS OF A REPLICATABLE RNA

[75] Inventors: Fred R. Kramer, New York, N.Y.; Paul M. Lizardi, Cuernavaca, Mexico

[73] Assignee: Gene-Trak Systems, Framingham, Mass.

[21] Appl. No.: 358,399

[22] Filed: May 26, 1989

[51] Int. Cl.$^5$ .................. C12Q 1/68; C07H 21/04
[52] U.S. Cl. .......................... 435/6; 435/91;
  435/172.3; 435/805; 436/501; 436/815; 536/27;
  935/2; 935/9; 935/17; 935/18; 935/19; 935/78;
  935/88
[58] Field of Search .............. 435/6, 91, 172.3, 805;
  436/501, 815; 536/27; 935/2, 9, 17, 18, 19, 78,
  88

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,786,600 | 11/1988 | Kramer et al. | 435/235 |
| 4,800,159 | 1/1989 | Mullis et al. | 435/172.3 |

FOREIGN PATENT DOCUMENTS

WO88/10315 12/1988 Int'l Pat. Institute.
WO89/01050 2/1989 Int'l Pat. Institute.

OTHER PUBLICATIONS

Miele (1982) Ph.D. Thesis, University Microfilms, Ann Arbor, Michigan.
Kwoh et al., *Proc. Natl. Acad. Sci. USA* 86:1173-1177 (Feb., 1989).
Miele et al., *J. Mol. Biol.*, 171:281-295 (1983).
Lizardi et al., *Bio/Technology* 6:1197-1202 (Oct. 1988).

*Primary Examiner*—Robert A. Wax
*Assistant Examiner*—Ardin H. Marschel
*Attorney, Agent, or Firm*—Hamilton, Brook, Smith & Reynolds

[57] ABSTRACT

This invention pertains to an improved method for detecting a nucleic acid target sequence with a replicatable RNA reporter system. Two polymerase-mediated reactions are used to generate a target-specific gene containing a DNA sequence for a replicatable RNA. Transcription of the target-specific gene yields a replicatable RNA which is amplified by replication. Synthesis of the gene and the replicatable RNA is strictly dependent upon specific interaction with the target sequence. Consequently, the amplified signal (RNA) is target-dependent and background signal is reduced.

66 Claims, 5 Drawing Sheets

TARGET-DEPENDENT SYNTHESIS OF AN ARTIFICIAL GENE FOR THE SYNTHESIS OF A REPLICATABLE RNA

BACKGROUND OF THE INVENTION

The use of nucleic acid hybridization probes for bioassays is well known. One of the early papers in the field directed to assays for DNA is Gillespie, D. and Spiegelman, S., "A Quantitative Assay for DNA-RNA Hybrids with DNA Immobilized on a Membrane", *J. Mol. Biol.* 12:829-842 (1965). In general, a nucleic acid hybridization assay involves separating the nucleic acid polymer chains in a sample, for example, by melting a sample of double stranded nucleic acid, affixing the separated nucleic acid strands to a solid surface such as a nitrocellulose membrane, and then introducing a detectable probe sequence which is complementary to a unique sequence to be detected (the "target" sequence) and incubating under appropriate conditions of stringency to allow the probe to hybridize to the complementary target sequence. Non-hybridized probes are removed by washing, and the amount of probe remaining is detected by one of a variety of techniques outlined below.

A recently developed nucleic acid hybridization assay involves the use of two probes, a first detectable target-specific probe and a second probe, often called a "capture probe". Ranki, M., Palva, A., Virtanen, M., Laaksonen, M., and Soderlund, H., "Sandwich Hybridization as a Convenient Method for the Detection of Nucleic Acids in Crude Samples", Gene 21:77-85 (1983); Syvanen, A. C., Laaksonen, M., and Soderlund, H., "Fast Quantification of Nucleic Acid Hybrids by Affinity-based Hyrid Collection", *Nucleic Acids Res.* 14:5037-5048 (1986). The capture probe contains a nucleic acid sequence which is complementary to the target sequence, preferably in a region near the sequence to which the first probe is complementary. The capture probe is provided with a means by which it can be bound to a solid surface. The hybridization of the capture probe and the sample nucleic acid can be carried out in solution, where it occurs rapidly, and the resulting hybrid can then be bound to a solid surface. One example of such a means for binding to a solid surface is biotin. Langer, P. R., Waldrop, A. A. and Ward, D. C., "Enzymatic Synthesis of Biotin-Labeled Polynucleotides: Novel Nucleic Acid Affinity Probes", *Proc. Natl. Acad. Sci.* U.S.A. 78:6633-6637 (1981). Through biotin, the capture probe can be bound to streptavidin linked to a solid support.

Several approaches have been used to detect target-specific probes. One approach is to link a detectable reporter group to the probe. Examples of such reporter groups are fluorescent molecules and $^{32}$P-labeled phosphate groups. Probe detection based upon these reporter groups has a practical limit of sensitivity of about one million targets per sample.

Another approach is to link a signal generating system to the probe. Examples are enzymes such as peroxidase. Enzyme-labeled probes are incubated with a chromogenic substrate and color formation is measured as indicative of the amount of probe. Leary, J. J., Brigati, D. J. and Ward, D. C., "Rapid and Sensitive Colorimetric Method for Visualizing Biotin-Labeled DNA Probes Hybridized to DNA or RNA Immobilized on Nitrocellulose: Bio-Blots", *Proc. Natl. Acad. Sci.* U.S.A. 80:4045-4049 (1983). The approach amplifies the detectable signal generated by a probe and enhances sensitivity of detection of target sequence molecules. As a practical matter, however, the nonspecific binding of probes has limited the improvement in sensitivity, compared to radioactive labeling, to roughly an order of magnitude, i.e., to a sensitivity of roughly 100,000 target molecules per sample Yet another approach to improving sensitivity of detection is to amplify the target sequence The amplification can be performed in vivo. See Hartley, J. L., Berninger, M., Jessee, J. A., Bloom, F. R. and Temple, G. S., "Bioassay for Specific DNA Sequences Using a Non-Radioactive Probe", *Gene* 49:295-302 (1986). The amplification can also be done in vitro using a technique called "polymerase chain reaction" (PCR). Saiki, R. K., Scharf, S., Faloona, F., Mullis, K. B., Horn, G. T., Erlich, H. A., and Arnheim, N., "Enzymatic Amplification of Beta-globin Genomic Sequences and Restriction Site Analysis for Diagnosis of Sickle Cell Anemia", *Science* 230:1350-1354 (1985); Saiki, R. K., Gelfand, D. H., Stoffel, S., Scharf, S. J., Higuchi, R., Horn, G. T., Mullis, K. B., and Erlich, H. A. "Primer-directed Enzymatic Amplification of DNA With a Thermostable DNA Polymerase", *Science* 239:487-491 (1988); Erlich, H. A., Gelfand, D. H., and Saiki, R. K., "Specific DNA Amplification", *Nature* 331:461-462 (1988); Guatelli, J. C. et. al., *Clin. Microbiol. Rev.* 2(2):217-226 (1989); and Mullis et al., European Patent Application Publication Nos. 200362 and 201184 (see also U.S. Pat. Nos. 4,683,195 and 4,683,202). In the PCR technique, a probe which is complementary only to the beginning of a target sequence is used. The probe serves as a primer for enzymatic replication of an entire target sequence. The replicative process is repeated and each repetition results in a doubling of the number of target sequences, until a large number of target sequences, for example, one million copies, are generated. Detectable probes can be used to detect the amplified number of targets. The PCR technique is very sensitive, but limited by the number of "false positive signals" generated, that is, the sequences generated that are not true copies of the target. The technique requires at least two nucleic acid probes and has three reaction steps for a single cycle.

Yet another method for improving sensitivity is to label the probe with an RNA that is copied in an exponential fashion by an RNA-directed RNA polymerase. An example of such a polymerase is the replicase of bacteriophage Q-beta. Haruna, I., and Spiegelman, S., "Autocatalytic Synthesis of a Viral RNA *In Vitro*", *Science* 150:884-886 (1965). Another example is brome mosaic virus replicase. March et al., *Positive Strand RNA Viruses* Alan R. Liss, N.Y. (1987). In this technique, the RNA label serves as a template for the exponential synthesis of RNA copies by the polymerase and thus, the amount of RNA is greatly amplified over the amount present initially. See Chu, B. C. F., Kramer, F. R., and Orgel, L. E., "Synthesis of an Amplifiable Reporter RNA for Bioassays", *Nucleic Acids Res.* 14:5591-5603 (1986); Lizardi, P. M., Guerra, C. E., Lomeli, H., Tussie Luna, I. and Kramer, F. R., "Exponential Amplification of Recombinant-RNA Hybridization Probes", *Bio/Technology* 6:1197-1203 (October 1988); European Patent Application 266,399 (EP Application No. 87903131.8).

Replication of the reporter RNA may take place while the RNA is linked to the probe or the replicatable RNA may be separated from the probe prior to replication. A variety of chemical linkage methods for joining the RNA to the probe may be employed. The probe sequence may be part of a replicatable recombinant RNA, as described in U S. Pat. No. 4,786,600, Lizardi. P. and Kramer. F. This recombinant RNA must be able to hybridize specifically with the target sequence and it must retain its ability to serve as a template for exponential replication by an appropriate RNA-directed RNA polymerase.

In practice, however, the sensitivity of this technique can be limited by the nonspecific binding of probes. Nonspecifically bound probe will lead to replication of the reporter RNA just as will probe which is hybridized specifically to the target. The signal produced by nonspecifically bound probes is commonly referred to as "back. ground", and its presence results in reduced sensitivity.

In U.S. patent application Ser. No. 251,696, Lizardi, P. et al., filed Sep. 30, 1988, a method is described for minimizing the background problem by exploiting allosteric features of a probe sequence. The 5' and 3' sequences flanking the probe are complementary while the central sequence is complementary to a target sequence. When the probe is bound specifically to a target sequence, the probe's self-complementary flanking sequences are separated from one another to form single-stranded regions which flank the double-stranded region formed between the probe's central sequence and the target nucleic acid. If, on the other hand, the probe is non-specifically bound, the probe's self-complementary 5' and 3' flanking sequences remain duplexed Specific detection of the probe target duplex is dependent on whether or not the self-complementary 5' and 3' flanking sequences are in a single stranded conformation.

Improved methods for eliminating or reducing the background signal attributable to the non specific binding of nucleic acid probes may lead to more sensitive hybridization assays and help to achieve the theoretical maximum sensitivity of such assays.

SUMMARY OF THE INVENTION

This invention pertains to an improved method for detecting a nucleic acid target sequence with a replicatable RNA reporter system. In the method of this invention, two probes serve as primers (refer red to herein as "probe-primers" to indicate their dual function of target-specific hybridization and of priming DNA polymerization in a complementary DNA synthesis reaction) for separate polymerase-mediated reactions that generate a target-specific gene containing a DNA sequence that then serves as a template for the synthesis a replicatable RNA. Transcription of the target-specific gene by a DNA-directed RNA polymerase yields a replicatable RNA which is exponentially amplified by an RNA. directed RNA polymerase. Because synthesis of the gene and the replicatable RNA is strictly dependent upon specific interaction of the probe-primers with the target sequence, the generation of an amplified signal (RNA) is target-dependent and thus background signal is reduced The target-specific gene is synthesized with two single-stranded oligonucleotide probes using standard gene cloning methods. In general, the first probe-primer is a DNA which comprises a promoter sequence and a sequence which is complementary to a first region of the target sequence and the second probe-primer is a DNA which comprises a sequence which corresponds to a second region of the target sequence. The second region of the target sequence is adjacent to, but not necessarily abutting, the first region of the target sequence. At least one of the probe-primers is linked to DNA that either corresponds to the sequence of a replicatable RNA or can serve as a template for transcription of a replicatable RNA. The exact nature of this sequence depends on the embodiment of the invention In one embodiment. DNA that can serve as a template for the synthesis of a non-interrupted replicatable RNA is linked to the second probe-primer. In another embodiment, DNA that corresponds to the sequence of a non-interrupted length replicatable RNA is located in the first probe-primer between the promoter sequence and the sequence complementary to the first region of the target. In another embodiment, DNA that corresponds to a sequence of a portion of a replicatable RNA is placed in the first probe-primer between the promoter sequence and the sequence complementary to the first region of the target and DNA that can serve as a template for the synthesis of the remainder of the replicatable RNA is placed in the second probe-primer. In other embodiments, DNA that can serve as a template for the synthesis of ribozyme sequences is incorporated into the second probe-primer either to achieve sequence, specific cleavage of the replicatable RNA from the transcript of the target specific gene or to destroy the replicatability of transcripts that contain a predetermined sequence.

In each of the embodiments, the first probe primer is hybridized to the first region of the target sequence and then extended on the template of the target sequence through at least the second region of the target sequence. The resulting extension product is separated from the target sequence. The second probe-primer is hybridized to the extension product and extended on the template of the extension product (in the anti-parallel direction) through the promoter sequence. This second extension results in the creation of a double-stranded DNA (a target-specific gene) with a functional double-stranded promoter that can direct transcription of the gene, thereby generating a replicatable RNA. The gene is then transcribed by a DNA-directed RNA polymerase to provide a replicatable RNA. The resulting RNA is then replicated by an RNA-directed RNA polymerase, and the replicated RNA is detected as indicative of the presence or the amount of target sequence.

BRIEF DESCRIPTION OF THE FIGURES

FIG. 1 illustrates an embodiment for target-dependent synthesis of a replicatable RNA having a copy of a target nucleic acid sequence at its 5' end.

FIG. 2 illustrates an embodiment for target-dependent synthesis of a replicatable RNA having a copy of a target nucleic acid sequence at its 3' end.

FIG. 3 illustrates an embodiment for target-dependent synthesis of a replicatable recombinant RNA which has a copy of a target nucleic acid sequence within it.

FIG. 4 illustrates an embodiment for target-dependent synthesis of a replicatable RNA having a copy of a target-nucleic acid sequence and a ribozyme at its 5' end which enables the 5' sequence to be cleaved from the replicatable RNA.

FIG. 5 illustrates an embodiment for target-dependent synthesis of a replicatable recombinant RNA having a copy of a target nucleic acid sequence within it, and a ribozyme at its 3' end which can cleave and thereby destroy the replicatable RNA if the copy of the target nucleic acid sequence contains a predetermined sequence.

DETAILED DESCRIPTION OF THE INVENTION

The nucleic acid hybridization assays of this invention are based on the specific generation of replicatable RNA molecules. The assays can be performed in two general ways, one which leads to the incorporation of the target nucleic acid sequences within a replicatable RNA molecule and one which does not. In a preferred embodiment, target-dependent synthesis of double-stranded DNA does not lead to the incorporation of target sequences into the replicatable RNA reporter. This embodiment is illustrated in FIG. 1.

In this embodiment, two oligonucleotide probe-primers are used. The first probe-primer is a single-stranded DNA molecule comprising (in 5' to 3' orientation) an RNA polymerase promoter sequence (p) and a sequence (a) complementary to a first region of the target sequence. The second probe-primer is a single-stranded DNA molecule comprising (in 3' to 5' orientation) a sequence (c') which corresponds to a second region of the target that is adjacent to, but not necessarily abutting, the first region of the target sequence (a'), and a DNA sequence that can serve as a template for the synthesis of a replicatable RNA (m'). As set forth below, the probe-primers are used to generate a target-specific gene in two primer-dependent extension reactions. The resulting artificial gene can then serve as a template for the synthesis of replicatable RNA.

In the first probe-primer, any promoter sequence can be used. Promoter sequences are generally about 20 nucleotides long. Preferred promoter sequences are strong promoters for the bacteriophage T7 RNA polymerase. Other suitable promoters include the bacteriophage Sp6 and T3 promoters and the *Escherichia coli* lac and trp promoters. The probe-primer sequences can be synthesized by an appropriate chemistry for nucleic acid synthesis (e.g., beta-cyanoethyl phosphoramidite chemistry) or they can be isolated from a biological source.

In general, probe-primer sequences which are either complementary or corresponding to regions of the target sequence should be sufficiently similar to the target sequences so that they hybridize to the sequence or its complement under suitable conditions without appreciable nonspecific hybridization.

In the first step of the (FIGS. 1A, 2A, 3A, 4A and 5A) method, the first probe-primer is hybridized to the first region of the target sequence (a'). (In the figure the target is shown as containing a region b' which represents the case where the first region of the target sequence (a') and second region of the target sequence (c') are not abutting). Suitable conditions for hybridization of the probe-primer are well-known to persons of ordinary skill in the art. The hybridized probe-primer is then extended on the template of the target sequence through the second region of the target sequence (c') to form an extension product (a b c). The probe primer serves to prime its own extension by a suitable polymerase. See e.g., Okayama and Berg, *Mol. Cell. Biol.* 2:161–170 (1982).

Depending on whether the target nucleic acid is DNA or RNA, a DNA-directed or an RNA-directed DNA polymerase, respectively, is used to synthesize the extension product (FIGS. 1B, 2B, 3B, 4B and 5B).

The extended portion of the first probe-primer is depicted by the dashed line. Examples of suitable polymerases include *E. coli* DNA polymerase I, the Klenow fragment of this enzyme, T4 DNA polymerase, Taq polymerase and reverse transcriptase. The extension reaction is performed by adding the appropriate polymerase and deoxyribonucleoside triphosphates to the sample reaction mixture. The reaction is allowed to proceed under standard conditions.

The newly synthesized extension product is then separated from the target sequence. This can be accomplished by any physical, chemical or enzymatic method of denaturing nucleic acid strands. A preferred method is heating the nucleic acid, generally to a temperature ranging from about 80° C. to 105° C.

After the strands are separated, the second probe-primer is hybridized to the extension product (FIGS. 1C, 2C, 3C, 4C and 5C). The second probe-primer comprises a sequence which corresponds to the second region of the target (c') and a DNA sequence that can serve as a template for the synthesis of a replicatable RNA (m'). The second probe-primer binds to the extended portion of the first probe primer at c. The second probe is extended on the template of the first extension product through the promoter sequence to generate a promoter complement (p') (FIGS. 1D, 2D, 3D, 4D and 5D). The extended portion of the second probe-primer is depicted as a dashed line. This results in the synthesis of a functional promoter for an RNA polymerase linked to a DNA that can serve as a template for the synthesis of a replicatable RNA. The promoter becomes active when joined with its complement to produce a double strand. See Milligan, J. F. et al., "Oligoribonucleotide Synthesis Using T7 RNA Polymerase and Synthetic DNA Templates" *Nucleic Acid Res.* 15:8783–8798 (1987). The functional joining of the two promoter complements is strictly dependent on each probe-primer interacting correctly with its region of the target. Thus, the two template-directed DNA extensions that give rise to transcriptionally active DNA are strictly de pendent on the sequential hybridization of the probe-primers to their target sequences.

The DNA is then transcribed, directed by the newly created promoter for an RNA polymerase, to produce a transcription product comprising a replicatable RNA having a copy of target sequence at its 5' end (FIGS. 1E, 2E, 3E, 4E and 5E). Conveniently, an RNA polymerase for transcription can be added along with the DNA polymerase used for extension of the second probe-primer so that transcription occurs instantly upon formation of the promoter by the second extension reaction.

The RNA polymerase for transcription is chosen in connection with a compatible promoter sequence. As mentioned above, a preferred RNA polymerase is the T7 RNA polymerase.

The next step is the amplification reaction in which the RNA is replicated by an RNA-directed RNA polymerase (RNA replicase). The conditions for use of replicase are well known in the art. See e.g., Kramer, F. R. et al, *J. Mol. Biol.* 89:719–736 (1974), Lizardi, P. M. et al. *Bio/Technology* 6:1197–1203 (1988).

Any replicatable RNA and its homologous RNA-directed RNA polymerase can be used in the method of this invention. The preferred replicatable RNA is a template for the RNA-directed RNA polymerase of bacteriophage Q-beta (Q-beta replicase) which is replicatable exponentially. Especially preferred is midivariant RNA (MDV.1 RNA; Kacian, D. L. *et al. Proc. Natl. Acad. Sci. U.S.A.* 69:3038-3042 (1972) or a mutant MDV-1 RNA (Kramer. F. R. *et al. supra*) These RNAs offer the advantage of being replicatable in recombinant form, thus permitting different embodiments of the invention that are described below. See Miele. E. A. *et al., J. Mol. Biol.* 171:281-295 (1983); U.S. Pat. No. 4,786,600. the teachings of which are incorporated by reference herein. MDV-1 RNA can be replicated with 3' or 5' extensions. permitting some of the additional embodiments described below. However, it is important to note that the 3' or 5' extensions are not copied during replication, and therefore there is no amplification of the target sequences.

Although the preferred embodiment for achieving amplification of replicatable RNA is the use of Q-beta replicase, amplification reactions can be achieved with other RNA replicases. Other useful replicases include other viral replicases such as the replicase of Brome Mosaic Virus.

The replicated RNA is then detected as indicative of the presence or the amount of target sequence. The RNA can be detected in a variety of different ways. For example, the replicatable RNA can be made fluorescent by, for example, a T4 RNA ligase catalyzed reaction which appends modified fluorescent nucleotides in the 3' end of a replicable RNA. See Cosstick *et al., Nucleic Acids Res.* 12, 1791 (1984). The fluorescence allows detection of the RNA by standard fluorescent detection techniques. Other methods that can be used to detect replicated RNA are those wherein a reporter substance that binds specifically to a nucleic acid is attached to the RNA and the signal generated thereby is detected. The reporter substance can be added to the reaction medium in which the RNA is replicated, or to a medium in which the RNA has been isolated such as a positively charged support such as ECTEOLA ™ paper. Such reporter substances include: chromogenic dyes, such as "stains all" (Dahlberg *et al., J. Mol. Biol.* 41, 139 (1969); methylene blue (Dingman et al., *Biochemistry* 7, 659 (1968), and silver stain (Sammons et al., *Electrophoresis* 2, 135 (1981); Igloi, *Anal. Biochem.* 134, 184 (1983); fluorogenic compounds that bind to RNA such as ethidium bromide or propidium iodide (Sharp et al., *Biochemistry* 12, 3055 (1973); Bailey et al., Anal. Biochem. 70, 75 (1976)) and fluorogenic compounds that bind specifically to RNAs that are templates for replication by the replicase, for example, a phycobiliprotein (Oi et al., *J. Cell Biol.* 93, 981 (1982); Stryer et al., U.S. Pat. No. 4,520,110) conjugated to the viral subunit of Q-beta replicase.

Figure 1A:
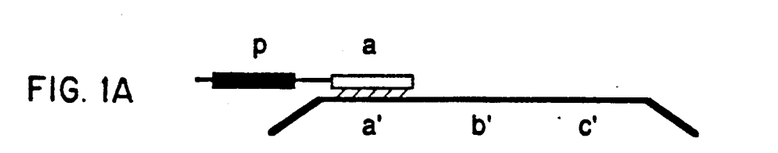
Figure 1B:
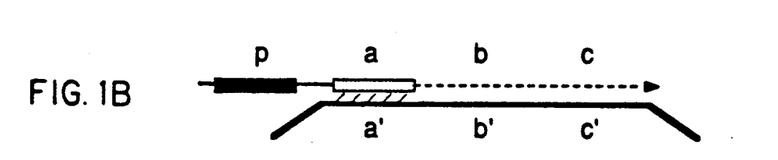
Figure 1C:
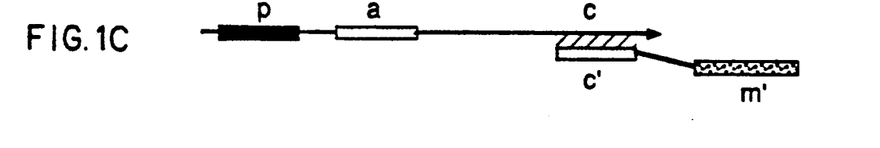
Figure 1D:
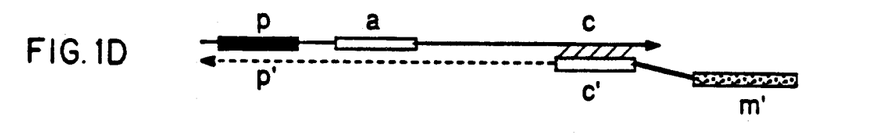
Figure 1E:
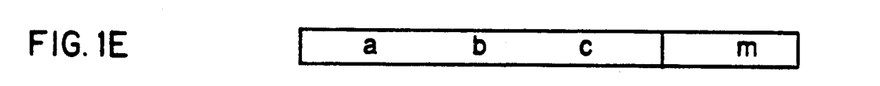
Figure 2A:
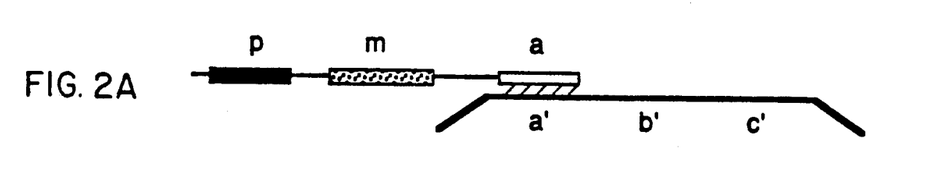
Figure 2B:
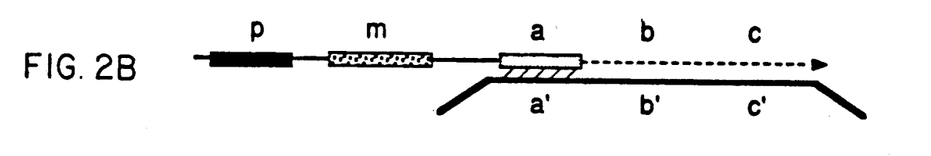
Figure 2C:
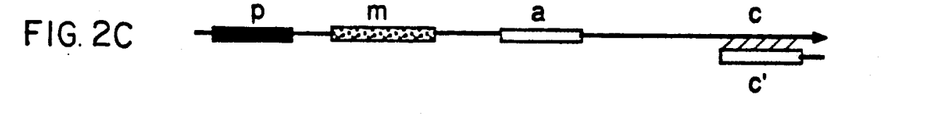
Figure 2D:
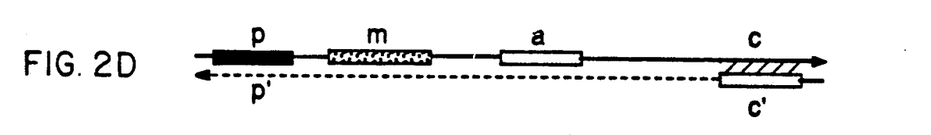
Figure 2E:
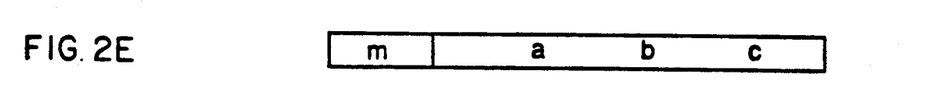

In a variation of this embodiment (FIG. 2), the first probe-primer comprises a promoter sequence (p), a DNA sequence corresponding to a non-interrupted replicatable RNA (m), and a DNA sequence (a) which is complementary to a first region of the target sequence. The second probe-primer comprises a DNA sequence which corresponds to the second region of the target sequence (c'). The first probe-primer is hybridized to the target sequence (FIG. 2A) and then extended with a DNA polymerase to produce an extension product (p m a b c; FIG. 2B). The extension product is separated and the second probe primer is hybridized to the extended portion of the first probe-primer (FIG. 2C). The second probe-primer is then extended with a DNA-directed DNA polymerase so that it contains a sequence complementary to the promoter sequence (FIG. 2D) This results in formation of a functional promoter linked to a template for a replicatable RNA molecule. Transcription yields a replicatable RNA (m) with a copy of the target sequence (a b c) at its 3' end (FIG. 2E). The transcript is replicated by an RNA replicase resulting in exponential synthesis of replicatable RNA that does not contain the copy of the target sequence.

Figure 3A:
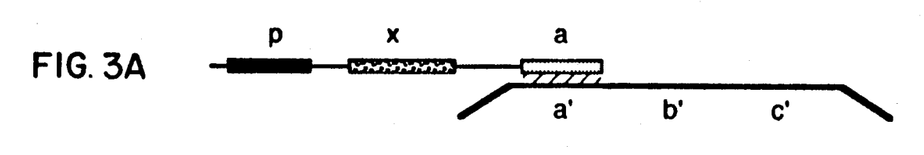
Figure 3B:
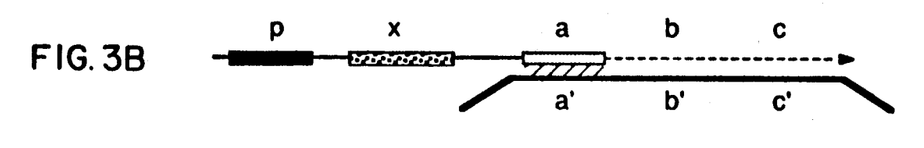
Figure 3C:
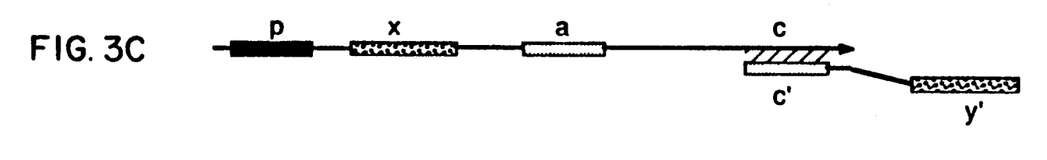
Figure 3D:
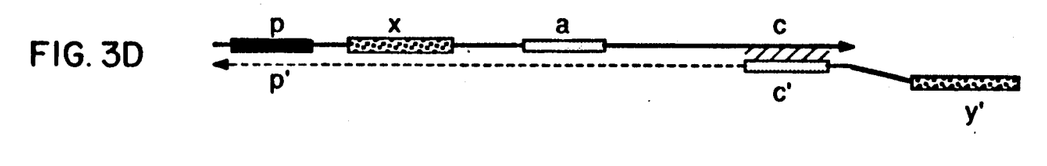
Figure 3E:
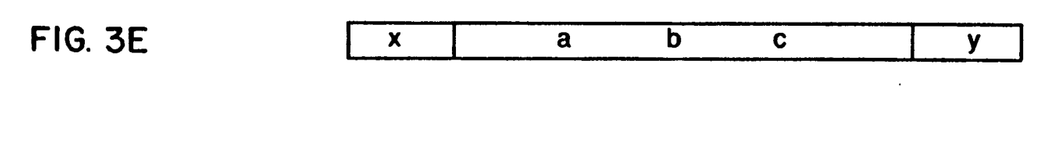
Figure 4A:
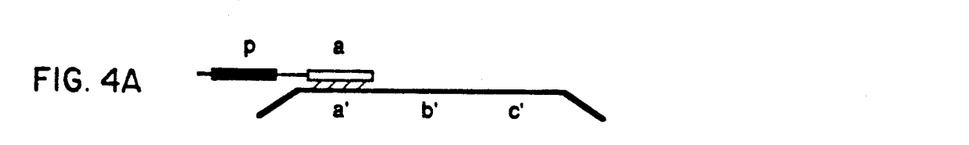
Figure 4B:
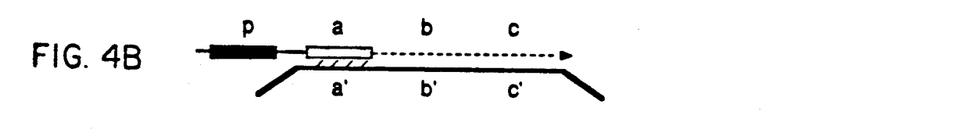
Figure 4C:
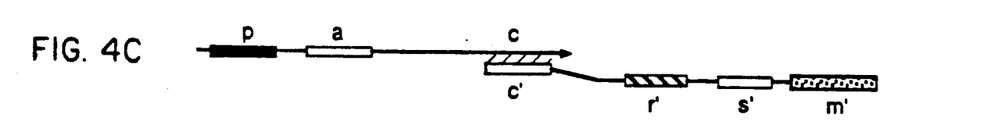
Figure 4D:
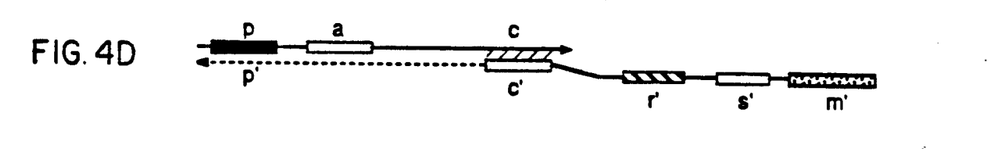
Figure 4E:
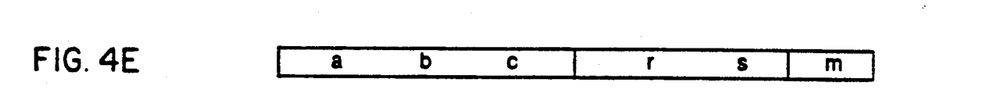
Figure 5A:
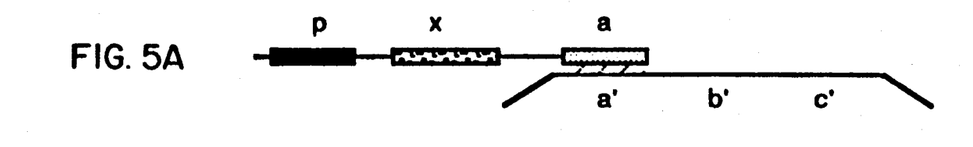
Figure 5B:
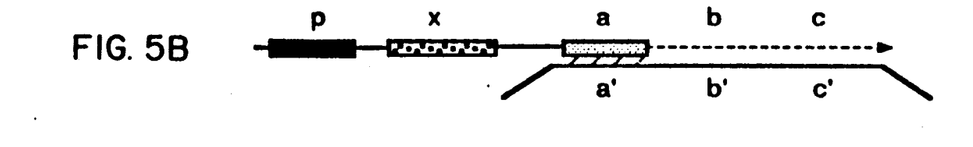
Figure 5C:
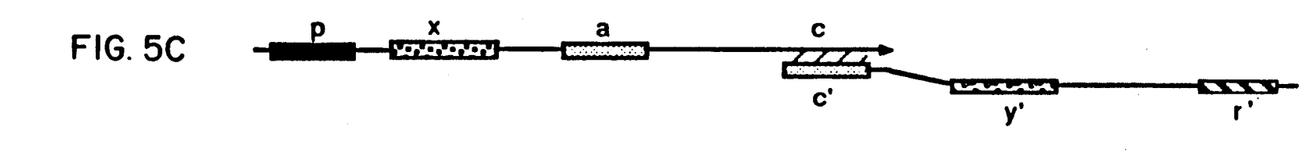
Figure 5D:
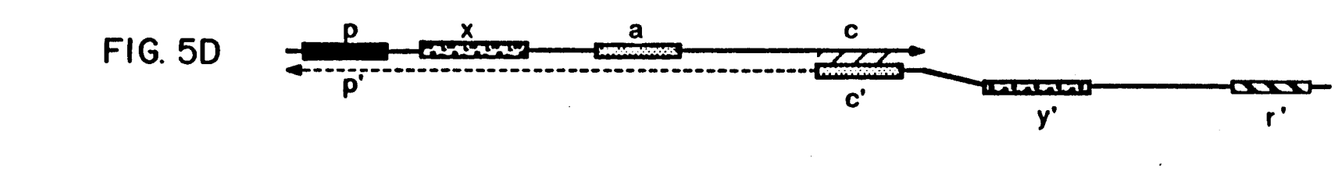
Figure 5E:
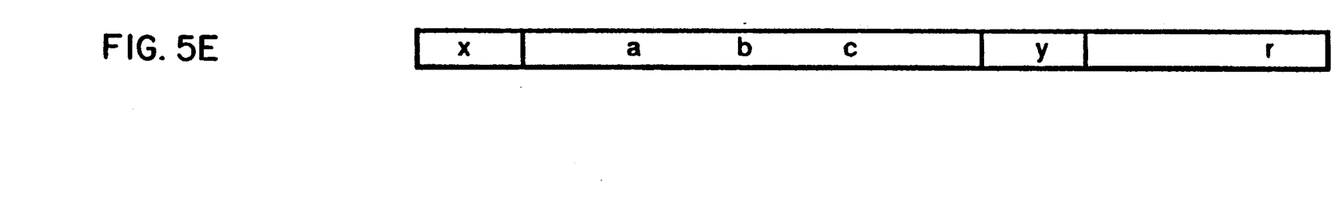

In another embodiment of the invention (illustrated in FIG. 3), the target-dependent synthesis of the artificial gene is designed to result in the incorporation of the target sequence into a replicatable RNA to yield a recombinant RNA molecule containing a sequence which is a copy of the target sequence. This embodiment involves the same basic principles as the previous embodiment, except that the composition of the first and second probes are different. The first probe-primer DNA contains (in 5' to 3' orientation) i) a promoter sequence (p), ii) a DNA sequence (x) corresponding to a portion of a replicatable RNA (e.g., 63 nucleotides at the 5' region of MDV-1 (+) RNA), and iii) a sequence (a) which is complementary to a first region of the target sequence. The second probe-primer contains (in 3' to 5' orientation ) a sequence which corresponds to a second region of the target sequence (c') and a DNA sequence (y') which is the complement of that portion of the replicatable RNA sequence that was not included in the first probe-primer (e.g., 157 nucleotides at the 3' region of MDV-1 (−) RNA). The two hybridization and primer extension steps (FIGS. 3A-3D) described above are performed to yield a DNA molecule comprising a functional promoter linked to a template for synthesis of a replicatable recombinant RNA that contains a copy of the target region (a b c) as an insert (FIG. 3E). When the transcripts are incubated with the RNA replicase the entire transcript is replicated.

Other embodiments of the invention involve the use of ribozymes which provide for specific cleavage of the RNA transcript. Ribozymes are regions of RNA molecules which interact and cleave other regions of an RNA molecule. A ribozyme sequence can be de signed to cleave a predetermined RNA sequence (a ribozyme recognition site). Uhlenbeck, O. C. *Nature* 328:590-600 (1987); Haseloff, J. and Gerlach, W. L. *Nature* 334:585-591 (1988). In general, the use of the ribozymes does not require any additional incubations or changes in buffer composition.

In one embodiment (FIG. 4), the first probe-primer comprises (in a 5' to 3' orientation) a promoter sequence (p) and a DNA sequence (a) complementary to a first region of a target sequence. The second probe-primer comprises (in a 3' to 5' orientation) a DNA sequence which corresponds to a second region of the target (c'), a DNA sequence that can serve as template for a ribozyme (r'), a DNA that can serve as a template for a ribozyme recognition site (s') and a DNA that can serve as a template for a replicatable RNA (m'). The ribozyme sequence is present in the DNA, but it is inactive (ribozymes are only active as RNA). The two hybridization and extension steps are performed (FIGS. 4A-4D) and the resulting artificial gene is transcribed. During the process of transcription, after the ribozyme recognition site is synthesized, the previously synthesized ribozyme catalyzes the cleavage of the RNA transcript at the ribozyme recognition site. As a result, the replicatable RNA is cleaved from the other parts of the transcript which can interfer with replication. Since MDV-1 RNAs with long extensions at their 5' or 3' ends are generally poor substrates for Q-beta replicase, the removal of the extensions provides a superior substrate for replication.

A refinement in the use of ribozymes enables discrimination between different allelic or other variants (e.g., mutations) of a nucleotide sequence (FIG. 5). For this purpose, the first probe-primer comprises, in 5' to 3' orientation, a promoter sequence (p), a DNA sequence that corresponds to a portion of a replicatable RNA (x) and a sequence (a) complementary to a first region of the target sequence adjacent to though not necessarily abutting a region of interest in the target (b'). The second probe-primer comprises a sequence that corresponds to a second region of the target (c'), and a DNA sequence which is the complement of the replicatable RNA sequence that was not included in the first probe-primer (y'), a spacer sequence and a DNA sequence which serves as a template for the synthesis of a ribozyme (r').

The two hybridization and extension steps are performed (FIGS. 5A-5D). Transcription yields a replicatable recombinant RNA that contains a copy of the target region as an insert and also contains a ribozyme at its 3' end and separated from the rest of the RNA by a spacer region. The ribozyme interacts with the predetermined region of interest if the sequence is a recognition site for the ribozyme. For example, the specificity of the ribozyme can be such that cleavage of the replicatable RNA occurs within the insert region only if a particular Predetermined variant sequence is present. This self-cleavage completely destroys the replicatability of the recombinant RNA. Nishihara, T. et al., *J. Biochem.* 93:669-674 (1983). In this way, signal generation is made dependent upon the presence or absence of a particular predetermined sequence that may vary by only one nucleotide.

The spacer is of sufficient length to permit the ribozyme to freely interact with the recognition site. This can be determined empirically. For MDV-1 RNA the spacer will typically be between 20-150 nucleotides in length.

In certain formats of the method, it may be desirable to immobilize any of the various nucleic acid constructs onto a solid phase. For example, the target-specific gene can be immobilized on a solid phase to separate it from the reaction medium after the second primer extension reaction. For this purpose, the probe-primers can be designed to contain elements for linkage to a solid phase. These elements include homopolymer tails and biotin molecules.

The reagents for performing the method of this invention can be assembled in kits. In general, a kit includes the following reagents in individual containers: a) the first and the second probe-primer according to any of the embodiments described above, b) a DNA polymerase and the four deoxyribonucleoside triphosphates for the primer extensions, c) a DNA-directed RNA polymerase and the four ribonucleoside triphosphates to transcribe the target specific gene. d) an RNA replicase to replicate the reporter RNA, and e) means for detecting the reporter RNA. A kit for detecting an RNA target sequence would include an RNA-directed DNA polymerase to perform the first primer extension reaction, whereas a kit for detecting a DNA target sequence would include a DNA-directed DNA polymerase to perform the first primer extension reaction. The kit can also include appropriate standards, buffers and wash solutions. Depending on the format of the method, additional components such as solid phase supports for immobilization of the nucleic acid constructs (e.g., the artificial gene or the replicated RNAs or both)

The method of this invention can be employed to detect any target nucleic acid sequences. The method can be used to detect specific genes, gene segments or RNA molecules. The assays are useful clinically, for, e.g., tissue, blood, and urine samples, as well as in food technology, agriculture, and biological research. Any source of nucleic acid, in purified or nonpurified form, can be utilized as a sample. The nucleic acid may be single- or double-stranded. Typically, the nucleic acid is extracted from a biological tissue or fluid This can be accomplished by standard techniques such as phenol extraction. Lizardi, P. (1983), *Method in Enzymology* 96:24-38.

If the nucleic acid to be tested is double-stranded, it is necessary to separate the strands so that one can function as a template. This can be done as a separate step or simultaneously with the synthesis of the primer extension products This strand separation can be accomplished by any suitable means for separation of nucleic acid strands, such as melting.

The method of this invention exploits the extraordinary level of amplification obtainable with replicatable RNA while eliminating the background problems associated with the use of simple replicatable probes. The method is fundamentally different from the PCR technique. In the PCR technique the target sequence is amplified by many cycles of primer extension. In the method of this invention the target nucleic acid itself is not amplified but rather utilized to synthesize a single copy of an artificial gene. Transcription of the gene generates a replicatable RNA. Amplification is obtained by exponential replication of the replicatable RNA. The amplification is strictly dependent on the synthesis of a target-specific gene. This strict dependency reduces background signal due to non-specific probe binding.

The invention is illustrated further by the following examples.

EXAMPLES

EXAMPLE I

1. Sample containing target nucleic acid (in this case. RNA) is prepared by a standard nucleic acid purification procedure, such as phenol extraction (See Lizardi. 1983, *Methods in Enzymology* 96:24-38).

2. After ethanol precipitation, the nucleic acid sample is dissolved in a solution containing 40 mM Tris HCl (pH 8.0), 10 mM $MgCl_2$, 5 mM dithiothreitol (DTT), 40 mM KCl, 60 μM of each deoxyribonucleoside triphosphate, 50 μg/ml bovine serum albumin, and reverse transcriptase. This solution also contains the FIRST PROBE-PRIMER, which comprises (from the 5' end): a T7 RNA polymerase promoter sequence followed by a DNA sequence complementary to a first region of the target. The sample is incubated for 1.5 minutes at 42° C., to allow for the synthesis of the first DNA extension product. Okayama and Berg. 1982, *Mol. Cell. Biol.* 2:161-170).

3. The sample is heated at 90° C. for 30 seconds, in order to release the first DNA extension product from the target nucleic acid.

4. The SECOND PROBE-PRIMER is added to the reaction. This probe-primer comprises (from the 3' end): a DNA sequence which corresponds to a second region of the target sequence and hybridizes to the DNA extension product, followed by a sequence that can serve as a template for the synthesis of a replicatable RNA that may be a recombinant sequence (Lizardi et al., 1988, *Biotechnology, supra*). DNA polymerase (Klenow fragment) is added, and the sample is incubated for 1.5 minutes at 42° C., in order to synthesize the complement of the first DNA extension product. This step completes the synthesis of the gene containing a phage RNA polymerase promoter followed by DNA that can be transcribed to yield a replicatable RNA.

5. T7 RNA polymerase and 400 μM of each ribonucleoside triphosphate are added to the sample (these components could also have been added at step 4). The sample is incubated for 10 minutes at 37° C., in order for transcription of the artificial gene to occur. The use of an SP6 phage promoter in an artificial gene is taught by Melton et al., 1984. Nucleic Acids Research, 12:7035-7056.

6. Q-beta replicase is added to the reaction, in order to replicate the transcription products generated in the previous step.

7. The amount of RNA generated by replication is measured by some means known to the art, such as the incorporation of a radioactive nucleotide, or staining with a fluorescent dye, such as ethidium bromide.

EXAMPLE II

The difference between this example and the first example is the composition of the FIRST and SECOND probe-primer.

1. Sample containing target nucleic acid (in this case, DNA) is prepared as described above.

2. The nucleic acid sample is dissolved in a solution containing 40 mM Tris-HCl (pH 8 0). 10 mM MgCL$_2$, 5 mM DTT, 40 mM KCl. 60 μM of each deoxyribonucleoside triphosphate, 50 μg/ml BSA, and the Klenow fragment of DNA polymerase I. This solution also contains the FIRST PROBE-PRIMER, which comprises (from the 5' end): a T7 RNA polymerase promoter sequence followed by a DNA sequence that can serve as a template for the synthesis of a replicatable RNA, and finally a DNA sequence complementary to a first region of the target sequence. The sample is incubated for 1.5 minutes at 37° C., to allow for the synthesis of the first DNA extension product.

3. The sample is heated at 90° C. for 30 seconds, in order to release the first DNA extension product from the target strand.

4. The SECOND PROBE-PRIMER is added to the reaction. This probe-primer comprises (from the 3' end): a DNA sequence which corresponds to a second region of the target sequence and hybridizes to the DNA extension product. The Klenow fragment of DNA polymerase is added, and the sample is incubated 1.5 minutes at 37° C., in order to synthesize the complement of the first DNA extension product. This step completes the synthesis of the gene containing a phage RNA polymerase promoter followed by DNA that can be transcribed to yield a replicatable RNA.

5. T7 RNA polymerase and 400 μM of each ribonucleoside triphosphate are added to the sample (these components could also have been added at step 4). The sample is incubated for 10 minutes at 37° C. in order for transcription of the artificial gene to occur.

6. Q-beta replicase is added to the reaction, in order to replicate the transcription products generated in the previous step.

7. The amount of RNA generated by replication is measured by the incorporation of a radioactive nucleotide, or by staining with a fluorescent dye, such as ethidium bromide.

EXAMPLE III

In this example, the FIRST and SECOND probe-primers are again different, and each contains a sequence that can serve as a template for the synthesis of a portion of a replicatable RNA. A copy of the target ultimately becomes part of the replicatable RNA reporter and is amplified by the replicase.

1. Sample containing target nucleic acid (in this case, DNA) is prepared as described above.

2. After ethanol precipitation the nucleic acid sample is dissolved in a solution containing 40 mM Tris-HCl (pH 8.0), 10 mM MgCl$_2$, 5 mM DTT, 40 mM KCl, 60 μM of each deoxyribonucleoside triphosphate. 50 μg/ml BSA. and the Klenow fragment of DNA polymerase. This solution also contains the FIRST PROBE-PRIMER, which comprises (from the 5' end): a T7 RNA polymerase promoter sequence, followed by a DNA sequence that corresponds to a portion of a replicatable RNA. and finally a DNA sequence complementary to a first region of the target sequence. The sample is incubated for 1.5 minutes at 42° C., to allow for the synthesis of the first DNA extension product.

3. The sample is heated at 90° C. for 30 seconds, in order to release the first DNA extension product from the target strand.

4. The SECOND PROBE-PRIMER is added to the reaction. This probe comprises (from the 3' end): DNA which corresponds to a second region of the target sequence and hybridizes to the first DNA extension product, followed by a sequence that can serve as a template for the synthesis of the remainder of the replicatable RNA sequence that was missing in the FIRST PROBE-PRIMER. The Klenow fragment of DNA polymerase is added, and the sample is incubated for 1.5 minutes at 42° C., in order to synthesize the complement of the first DNA extension product. This step completes the synthesis of the gene containing a phage RNA polymerase promoter followed by a DNA sequence that can be transcribed to yield a replicatable RNA. During the process of synthesis, the gene has incorporated target sequences. The resulting artificial gene can serve as a template for the synthesis of a recombinant RNA which includes a copy of the target sequence.

5. T7 RNA polymerase and 400 μM of each ribo nucleoside triphosphate are added to the sample (these components could also have been added at step 4). The sample is incubated for 10 minutes at 37° C. in order for transcription of the artificial gene to occur 6. Q-beta replicase is added to the reaction, in order to replicate the transcription products generated in the previous step.

7. The amount of RNA generated by replication is measured by some means known to the art, such as the incorporation of a radioactive nucleotide, or staining with a fluorescent dye, such as ethidium bromide.

METHODS INVOLVING RIBOZYMES

The method involving the use of ribozymes can be implemented using the methods described in Examples I-III with minor modifications that allow the ribozymes to operate as in the cited references.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method of detecting a target nucleic acid sequence, comprising the steps of:
   a) hybridizing a first single-stranded oligodeoxynucleotride probe-primer to a first region of the target sequence, the first probe-primer having a 5' portion comprising a promoter sequence and a 3' portion comprising a sequence complementary to the first region of the target sequence;
   b) extending the probe-primer on the template of the target sequence through a second region of the target sequence which is adjacent to, though not necessarily abutting, the first region of the target sequence, to produce a DNA extension product;
   c) separating the DNA extension product from the target sequence;
   d) hybridizing a second oligodeoxynucleotide probe-primer to the DNA extension product, the second probe-primer having a 5' portion comprising a DNA sequence that can serve as a template for the synthesis of a replicatable RNA and a 3' portion comprising a sequence complementary to the complement of the second region of the target sequence which is present in the DNA extension product;
   e) extending the second probe-primer on the template of the DNA extension product to produce a double-stranded DNA comprising a functional double-stranded promoter and DNA that can serve as a template for the synthesis of a replicatable RNA;
   f) transcribing the DNA to produce a replicatable RNA;
   g) replicating the RNA; and
   h) detecting the replicated RNA as indicative of the presence or the amount of the target nucleic acid sequence.

2. A method of claim 1, wherein the promoter sequence of the first probe-primer is a T7 RNA polymerase promoter.

3. A method of claim 1, wherein the first and second probe-primer are extended by a DNA polymerase.

4. A method of claim 3, wherein the target nucleic acid sequence is a DNA sequence and the first and second probe-primers are extended by a DNA-directed DNA polymerase.

5. A method of claim 4, wherein the DNA-directed DNA polymerase is *Escherichia coli* polymerase I or the Klenow fragment thereof, or Taq polymerase.

6. A method of claim 3, wherein the target nucleic acid sequence is RNA and the first probe-primer is extended by an RNA-directed DNA polymerase.

7. A method of claim 1, wherein the DNA extension product is separated from the target sequence by heat denaturation.

8. A method of claim 1, wherein the transcription step is performed with T7 RNA polymerase, T3 RNA polymerase or SP6 RNA polymerase.

9. A method of claim 1, wherein the replicatable RNA is a template for an RNA-directed RNA polymerase.

10. A method of claim 9, wherein the replicatable RNA is a template for the replicase of bacteriophage Q-beta.

11. A method of claim 10, wherein the replicatable RNA is midivariant RNA.

12. A method of claim 1, wherein the replicated RNA is detected by ethidium bromide or propidium iodide staining.

13. A method of detecting a target nucleic acid sequence, comprising the steps of:
   a) hybridizing a first single-stranded oligodeoxynucleotide probe-primer to a first region of the target sequence, the first probe-primer having a 5' portion comprising a promoter sequence, a DNA sequence that encodes a replicatable RNA and a 3' portion comprising a DNA sequence complementary to the first region of the target sequence;
   b) extending the first probe-primer on the template of the target sequence through a second region of the target sequence which is adjacent to, though not necessarily abutting, the first region of the target sequence, to produce a DNA extension product;
   c) separating the extension produce from the target sequence;
   d) hybridizing a second oligodeoxynucleotide probe-primer to the DNA extension product, the second probe-primer having a 3' terminus comprising a sequence complementary to the complement of the second region of the target sequence which is present in the DNA extension product;
   e) extending the second probe-primer on the template of the extension product to produce a double-stranded DNA comprising a functional double-stranded promoter and DNA that can serve as a template for synthesis of a replicatable RNA;
   f) transcribing the DNA to produce a replicatable RNA;
   g) replicating the RNA; and
   h) detecting the replicated RNA as indicative of the presence or the amount of the target nucleic acid sequence.

14. A method of claim 13, wherein the promoter sequence of the first probe-primer is a T7 RNA polymerase promoter.

15. A method of claim 13, wherein the first and second probe-primers are extended by a DNA polymerase.

16. A method of claim 13, wherein the target nucleotide sequence is a DNA sequence and the first and second probe-primer are extended by a DNA-directed DNA polymerase.

17. A method of claim 16, wherein the DNA-directed DNA polymerase is *Escherichia coli* polymerase I or the Klenow fragment thereof or Taq polymerase.

18. A method of claim 13, wherein the extension product is separated from the target sequence by heat denaturation.

19. A method of claim 13, wherein the transcription step is performed with T7 RNA polymerase. T3 RNA polymerase or SP6 RNA polymerase.

20. A method of claim 13, wherein the replicatable RNA is a template for an RNA-directed RNA polymerase.

21. A method of claim 20, wherein the replicatable RNA is a template for the replicase of bacteriophage Q-beta.

22. A method of claim 21, wherein the replicatable RNA is midivariant RNA.

23. A method of claim 13, wherein the replicated RNA is detected by ethidium bromide or propidium iodide staining.

24. A method of detecting a target nucleic sequence, comprising the steps of:
a) hybridizing a first single-stranded oligodeoxynucleotide probe-primer to a first region of the target sequence, the first probe-primer having a 5' portion comprising a promoter sequence, a DNA sequence that corresponds to about 63 nucleotides from the 5' terminus of midivariant RNA and a 3' portion complementary to the first region of the target sequence;
b) extending the first probe-primer on the template of the target sequence through a second region of the target sequence which is adjacent to, through not necessarily abutting, the first region of the target sequence, to produce a DNA extension product;
c) separating the extension product from the target sequence;
d) hybridizing a second oligodeoxynucleotide probe-primer to the extension product, the second probe-primer having a 5' portion comprising a DNA sequence which is the complement of the portion of the midivariant RNA sequence that was not included in the first probe-primer and a 3' portion comprising a nucleotide sequence which is complementary to the complementary of the second region of the target sequence;
e) extending the second probe-primer on the template of the extension product to produce a double-stranded DNA comprising a functional double-stranded promoter and DNA that can serve as a template for the synthesis of a replicatable RNA containing a copy of the target sequence inserted within;
f) transcribing the DNA to produce a replicatable recombinant RNA;
g) replicating the RNA; and
h) detecting the replicated RNA as indicative of the presence or the amount of the target nucleic acid sequence.

25. A method of claim 24, wherein the promoter sequence of the first probe-primer is a T7 RNA polymerase promoter.

26. A method of claim 24, wherein the first and second probe-primers are extended by a DNA polymerase.

27. A method of claim 24, wherein the target nucleic acid sequence is a DNA sequence and the first and second probe-primer are extended by a DNA-directed DNA polymerase.

28. A method of claim 27, wherein the DNA-directed DNA polymerase is *Escherichia coli* polymerase I or the Klenow fragment thereof, or Taq polymerase.

29. A method of claim 24, wherein the target nucleic acid sequence is an RNA sequence and the first probe-primer is extended by an RNA-directed-DNA polymerase.

30. A method of claim 24, wherein the extension product is separated from the target sequence by heat denaturation.

31. A method of claim 24, wherein the replicatable RNA is a template for an RNA-directed RNA polymerase.

32. A method of claim 31, wherein the replicatable RNA is a template for the replicas of bacteriophage Q-beta.

33. A method of claim 24, wherein the replicated RNA is detected by ethidium bromide or propidium iodide staining.

34. A method of detecting a target nucleotide sequence, comprising the steps of:
a) hybridizing a first single-stranded oligodeoxynucleotide probe-primer to a first region of the target sequence, the first probe-primer having a 5' portion comprising a promoter sequence and a 3' portion comprising a sequence complementary to the first region of the target sequence;
b) extending the probe-primer on the template of the target sequence through a second region of the target sequence which is adjacent to, but not necessarily abutting, the first region, to produce a DNA extension product;
c) separating the DNA extension product from the target sequence;
d) hybridizing a second oligodeoxynucleotide probe-primer to the DNA extension product, the second probe-primer comprising, in order from the 3' end to the 5' end,
   i) a DNA sequence complementary to the complement of the second region of the target sequence which is present in the DNA extension product;
   ii) a DNA that can serve as a template for the synthesis of a ribozyme;
   iii) a DNA sequence that can serve as a template for the synthesis of a ribozyme recognition site; and
   iv) a DNA sequence that serves as a template for the synthesis of a replicatable RNA;
e) extending the second probe-primer on the template of a DNA extension product to produce a double-stranded DNA extension product comprising a functional double-stranded promoter and DNA that can serve as a template for the synthesis of a replicatable RNA having a ribozyme, a ribozyme recognition site, and a copy of the target sequence at its 5' end;
f) transcribing the DNA to produce an RNA transcript having a functional ribozyme, a ribozyme recognition site and a replicatable RNA, the ribozyme being capable of cleaving the transcript at the recognition site to release the replicatable RNA;
g) replicating the RNA; and
h) detecting the replicated RNA as indicative of the presence or the amount of the target nucleotide sequence.

35. A method of claim 34, wherein the promoter sequence of the first probe-primer is T7 RNA polymerase promoter.

36. A method of claim 34, wherein the first and second probe-primer are extended by a DNA polymerase.

37. A method of claim 36, wherein the target nucleic acid sequence is a DNA sequence and the first and second probe-primer are extended by a DNA-directed DNA polymerase.

38. A method of claim 37, wherein the DNA-directed DNA polymerase is *Escherichia coli* polymerase I or the Klenow fragment thereof, or Taq polymerase.

39. A method of claim 34, wherein target nucleotide sequence is RNA and the first probe-primer is extended by an RNA-directed DNA polymerase.

40. A method of claim 34, wherein the DNA extension product is separated from the target sequence by heat denaturation.

41. A method of claim 34, wherein the transcription step is performed with T7 RNA polymerase, T3 RNA polymerase or SP6 RNA polymerase.

42. A method of claim 34, wherein the replicatable RNA is a template for an RNA-directed RNA polymerase.

43. A method of claim 42, wherein the replicatable RNA is a tmplate for the replicase of bacteriophage Q-beta.

44. A method of claim 43, wherein the replicatable RNA is midivariant RNA.

45. A method of claim 34, wherein the replicated RNA is detected by ethidium bromide or propidium staining.

46. A method of detecting a target nucleotide sequence, comprising the steps of:
  a) hybridizing a first single-stranded oligodeoxynucleotide probe-primer to a first region adjacent to the target sequence, the first probe-primer having a 5' portion comprising a promoter sequence, an internal DNA sequence that corresponds to a portion of a replicatable RNA and a 3' portion comprising a sequence complementary to the first region of the target sequence;
  b) extending the probe-primer through a second region of the target sequence which is adjacent to, but not necessarily abutting, the first region of the target sequence, to produce a DNA extension product;
  c) separating the DNA extension product from the target sequence;
  d) hybridizing a second oligodeoxynucleotide probe-primer to the DNA extension product, the second probe-primer having a 3' portion comprising a DNA sequence complementary to the complement of the second region of the target sequence which is present in the DNA extension product, a DNA sequence that can serve as a template for the synthesis of the remainder of the replicatable RNA, and a DNA sequence that can serve as a template for the synthesis of a ribozyme that can bind and cleave a predetermined RNA sequence;
  e) extending the second probe-primer on the template of the DNA extension product to produce a double-stranded DNA comprising a functional double-stranded promoter and DNA that can serve as a template for the synthesis of a replicatable RNA containing a copy of the target sequence inserted within it and containing a ribozyme at its 3' end;
  f) transcribing the DNA to produce a replicatable recombinant RNA which can be cleaved by the ribozyme if it contains the predetermined sequence in the copy of target sequence;
  g) replicating the RNA; and
  h) detecting the replicated RNA as indicative of the presence or absence of the predetermined sequence in the target sequence.

47. A method of claim 46, wherein the predetermined sequence within the copy of the target sequence is an allelic variant.

48. A method of claim 46, wherein the promoter sequence of the first probe-primer is T7 RNA polymerase promoter.

49. A method of claim 46, wherein the first and second probe-primer are extended by a DNA polymerase.

50. A method of claim 49, wherein the target nucleotide sequence is a DNA sequence and the first and second probe-primer are extended by a DNA-directed DNA polymerase.

51. A method of claim 48, wherein the DNA-directed DNA polymerase is Escherichia coli polymerase 1 or the Klenow fragment thereof, or Taq polymerase.

52. A method of claim 44, wherein target nucleotide sequence is RNA and the first probe-primer is extended by an RNA-directed DNA polymerase.

53. A method of claim 44, wherein the DNA extension product is separated from the target sequence by heat denaturation.

54. A method of claim 46, wherein the transcription step is performed with T7 RNA polymerase, T3 RNA polymerase or SP6 RNA polymerase.

55. A method of claim 51, wherein the replicatable RNA is a template for an RNA-directed RNA polymerase.

56. A method of claim 52, wherein the replicatable RNA is a template for the replicase of bacteriophage Q-beta.

57. A method of claim 53, wherein the replicatable RNA is midivariant RNA

58. A method of claim 44, wherein the replicated RNA is detected by ethidium bromide or propidium iodide staining.

59. A combination of oligodeoxynucleotides for use in detecting a target nucleic acid sequence, comprising:
  a) a first oligodeoxynucleotide having a 5' portion comprising a promoter sequence and a 3' portion comprising a sequence complementary to a first region of the target nucleotide sequence; and
  b) a second oligodeoxynucleotide having a 5' portion comprising a DNA sequence that can serve as a template for the synthesis of a replicatable RNA and a 3' portion comprising a DNA sequence complementary to the complementary of a second region of the target sequence which is adjacent to, but not necessarily abutting, the first region of the target sequence.

60. A combination of oligonucleotides of claim 59, wherein the promoter is for T7 RNA polymerase.

61. A combination of oligonucleotides claim 59, wherein the replicatable RNA is a template for the replicase of bacteriophage Q-beta.

62. A combination of oligodeoxynucleotides for use in detecting a target nucleotide sequence, comprising:
  a) a first oligodeoxynucleotide having a 5' portion comprising a promoter sequence, a DNA sequence that encodes a replicatable RNA and having a 3' portion comprising a sequence complementary to a first region of the target sequence; and
  b) a second oligodeoxynucleotide comprising a sequence complementary to the complement of a second region of the target nucleotide sequence.

63. A combination of oligodeoxynucleotide of claim 62, wherein the promoter is for T7 RNA polymerase.

64. A combination of oligodeoxynucleotides of claim 63, wherein the replicatable RNA is a template for the replicase of bacteriophage Q-beta.

65. A combination of oligonucleotides for use in detecting a target nucleic acid sequence, comprising:
  a) a first oligodeoxynucleotide having a 5' portion comprising a promoter sequence and having a 3' portion comprising a sequence complementary to a first region of the target sequence; and
  b) a second oligodeoxynucleotide having a 5' portion comprising, in order from the 3' end to the 5' end, i) a DNA sequence complementary to the complement of a second region of the target sequence;
ii) a DNA that can serve as a template for the synthesis of a ribozyme;
iii) a DNA sequence that can serve as a template for the synthesis of a ribozyme recognition site; and
iv) a DNA sequence that serves as a template for the synthesis of a replicatable RNA.

66. A combination of oligodeoxynucleotides for use in detecting a predetermined nucleotide sequence in target nucleic acid sequence, comprising:

a) a first oligodeoxynucleotide having a 5' portion comprising a promoter sequence, a DNA sequence encoding about 63 bases of the 5' end of midivariant RNA and having a 3' portion comprising a sequence complementary to a first region of the target sequence;

b) a second oligodeoxynucleotide having a 5' portion comprising a DNA sequence that can serve as a template for the synthesis of the remainder of the midivariant RNA, a DNA sequence complementary to the complement of a second region of the target sequence and a DNA sequence that can serve as a template for the synthesis of a ribozyme that can bind and cleave the predetermined RNA sequence.

* * * * *